United States Patent
Sulya (10) Patent No.: US 10,585,095 B2
(45) Date of Patent: Mar. 10, 2020

(54) SYSTEMS AND METHODS FOR BIOPROCESS ANALYSIS

(71) Applicant: Circle Technologies, Inc., Tulalip, WA (US)

(72) Inventor: Andrew Sulya, Tulalip, WA (US)

(*) Notice: Subject to any disclaimer, the term of this patent is extended or adjusted under 35 U.S.C. 154(b) by 484 days.

(21) Appl. No.: 14/905,739

(22) PCT Filed: Jul. 18, 2014

(86) PCT No.: PCT/US2014/047312
§ 371 (c)(1),
(2) Date: Jan. 15, 2016

(87) PCT Pub. No.: WO2015/010097
PCT Pub. Date: Jan. 22, 2015

(65) Prior Publication Data
US 2016/0161478 A1   Jun. 9, 2016

Related U.S. Application Data

(60) Provisional application No. 61/856,535, filed on Jul. 19, 2013.

(51) Int. Cl.
G01N 33/543 (2006.01)
C12M 1/34 (2006.01)
B01D 15/38 (2006.01)

(52) U.S. Cl.
CPC ... G01N 33/54386 (2013.01); B01D 15/3809 (2013.01); C12M 41/32 (2013.01)

(58) Field of Classification Search
None
See application file for complete search history.

(56) References Cited

U.S. PATENT DOCUMENTS

| | | | |
|---|---|---|---|
| 5,571,720 A | 11/1996 | Grandics et al. | |
| 5,711,888 A | 1/1998 | Trampler et al. | |
| 2004/0033562 A1 | 2/2004 | Miller | |
| 2004/0259240 A1* | 12/2004 | Fadden | C12M 47/10 435/297.3 |
| 2006/0194313 A1* | 8/2006 | Pierce | B01D 61/16 435/325 |
| 2006/0240550 A1* | 10/2006 | Goodwin | C12M 27/10 435/325 |
| 2010/0317093 A1 | 12/2010 | Turewicz et al. | |

FOREIGN PATENT DOCUMENTS

WO   2015/010097 A2   1/2015

OTHER PUBLICATIONS

Siegel et al., "Spin Filter for Continuous Perfusion of Suspension Cells". Ed. Spier, R.E., Griffiths, J.B., MacDonald, C., Oxford: Butterworth-Heinemann Ltd. 1992. p. 434-436 (Year: 1992).*
International Search Report of PCT/US2014/047312, filed Jul. 18, 2014, ISR dated Jan. 22, 2015.

* cited by examiner

*Primary Examiner* — Christine Foster
*Assistant Examiner* — Ellen J Marcsisin (57) ABSTRACT

Disclosed herein are systems, methods, and devices for monitoring and controlling bioprocess parameters. The systems and methods enable automated operation with real-time analysis of process conditions and analyte or biologic production.

18 Claims, 5 Drawing Sheets

SYSTEMS AND METHODS FOR BIOPROCESS ANALYSIS

CROSS REFERENCE TO RELATED APPLICATIONS

This application is a 371 of PCT/US2014/047312, filed Jul. 18, 2014, 2014, which claims benefit under 35 U.S.C. § 119(e) from U.S. Provisional Patent Application Ser. No. 61/856,535, filed Jul. 19, 2013, the content of which is incorporated herein by reference in its entirety.

TECHNICAL FIELD

The present specification relates to articles and methods useful for giving real-time analyte concentration measurements or titer in fermentation bioreactors.

BACKGROUND

Current trends in the pharmaceutical industry are toward the development of antibody and other protein-based pharmaceuticals. These drugs have the advantage of selectively targeting binding sites in the body. The drugs, sometimes classified as "biologics," are often produced by cell cultures in fermentation reactors with volumes ranging from of 3 L to 10000 L. To prevent the growth of foreign cells or pathogens, the sterility of the reactor must be maintained at all times. Therefore, real time analysis of the reactor contents and characteristics is limited, as the time and labor required to gather samples and generate data, results in an information gap; typically meaningful data can take hours or days to develop.

Further, current devices capable of maintaining sterility and quantifying the drug, nutrient metabolites and or other analytes as the fermentation progresses are limited in that they can only measure these when the concentrations are high. Current devices capable of maintaining sterility and quantifying the nutrient levels as the fermentation progresses are limited in that they can only measure the nutrient levels at the beginning of the batch when the concentration are high. This causes windows of time when the analyte levels are not measurable.

SUMMARY

Aspects disclosed herein comprise systems, devices, and methods for direct real-time measurements of process characteristics and/or analytes such as biologics as they are being generated. In an embodiment the system is self-contained and automated and can make fully automated accurate measurements throughout the fermentation process.

In an embodiment the system comprises
a growth vessel;
a sampling system;
a filtration system;
a cartridge with a stationary phase;
a analyte detection system;
a collector;
and a processor.

In an aspect the system can further comprise sterile prefilled solvent reservoirs.

In an aspect the system can further comprise a pumping system.

In an aspect the system can further comprise a multiport valve.

In an aspect the system can further comprise prefilled syringes.

In an embodiment the stationary phase can comprise affinity chromatography resin.

In an aspect the system can further comprise a collector comprising a vial containing a buffer solution that collects analyte material.

In an aspect the system can further comprise an optical detector.

In an aspect the system can further comprise a pumping system that is a multichannel pump or multiple pumps.

Disclosed aspects include methods for determining real-time analyte concentration measurements from fermentation liquid, comprising:
producing analyte or analytes in a growth vessel;
sampling and filtering analyte or analytes in a sampling system;
removing and loading analyte or analytes onto a cartridge with affinity chromatography stationary phase;
collecting analyte data;
computing and calculating to correct for buffer background;

In an aspect the method can further comprise transmitting the data to a server.

In an aspect the method can further comprise adjusting system parameters based on the collected data.

In an aspect the method can further comprise injecting a solution of a known concentration of analyte into the system to calibrate or check calibration of the instrument and detection system.

BRIEF DESCRIPTION OF THE DRAWINGS

FIG. 3 is a detailed design schematic of system components. In this embodiment syringe pumps are used to deliver reagents like wash and elution buffer. Sample is loaded onto a cartridge, washed and removed to a detector which gives a peak response. The purified analyte is collected and stored in refrigerated or frozen conditions.

FIG. 4 is a detailed design schematic of the flow path of the system. In this embodiment, the sample is collected, filtered and analyzed by the Circle Technologies PAT system. Syringe pumps are used to deliver reagents and standard solutions. The purified sample is collected and data passed to a process controller.

FIG. 5 is a detailed design schematic of system components. In this embodiment the sample containing cells analytes and growth media is pumped into a filtration system. Cells in a reduced volume of growth media can be returned to the bioreactor in a closed sterile loop. In this embodiment a multichannel peristaltic pump is used to deliver reagents like wash and elution buffer and a standard solution for calibration.

FIG. 6 is a detailed design schematic of the filter system. A cylindrical filter allows growth media, biologic drugs and analytes of interest to pass through the filter. Cells in a reduced volume of growth media can be returned to the bioreactor in a closed sterile loop. In some embodiments the filter is rotated at 3600 rpm via an attached cam. The rotation serves to keep the filter surface clean and provide centrifugal force to keep the cells away from the filter surface, extending the lifetime of the filter to operate without needing to be changed until the entire batch is completed.

DETAILED DESCRIPTION

Figure 1:
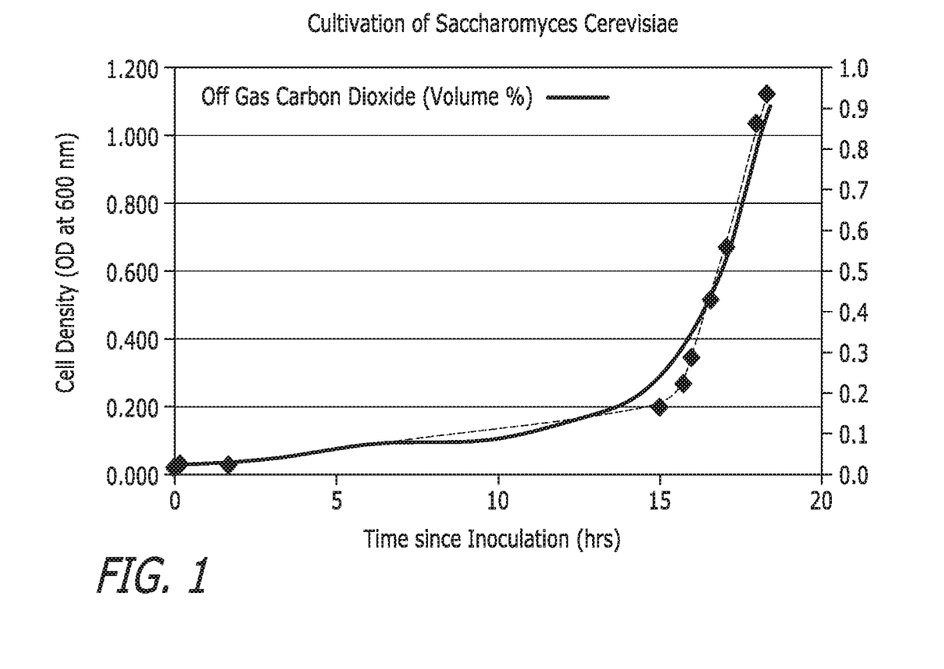
FIG. 1 shows cultivation of *saccharomyces cerevisiae*, graphing cell density and carbon dioxide produced with respect to time since inoculation. Current trends are to assume that the cell density and carbon dioxide levels are correlated with the drug concentration. However, in cases where cells mutate and produce less drug or when foreign cell bodies are present in the bioreactor, then the cell density can have little or no correlation with drug levels.
Figure 2:
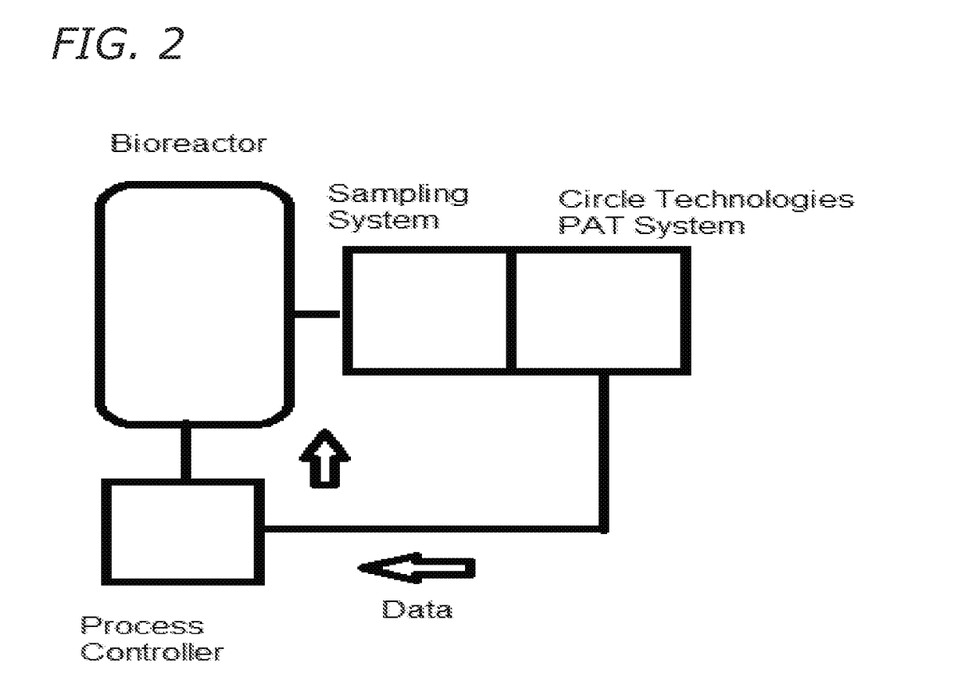
FIG. 2 is a detailed design schematic of the flow path of the system In this embodiment, the sample is collected by an external sampling system. Syringe pumps are used to deliver reagents and standard solutions. The purified sample is collected and data passed to a process controller.
Figure 3:
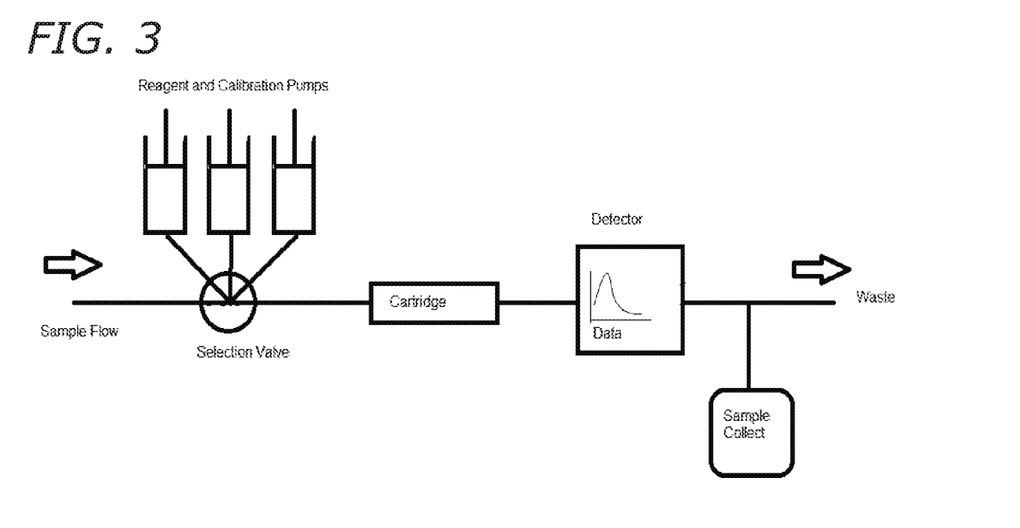
Figure 4:
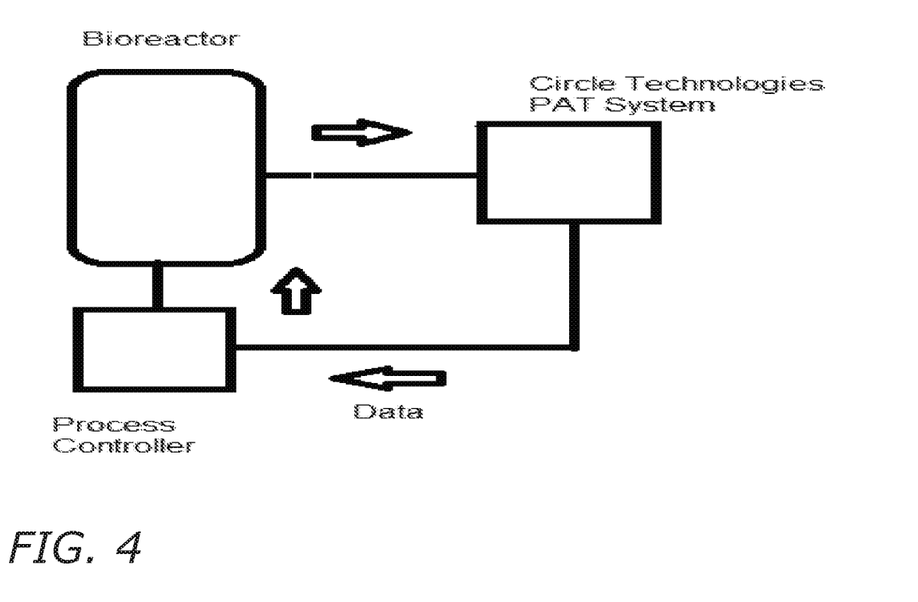
Figure 5:
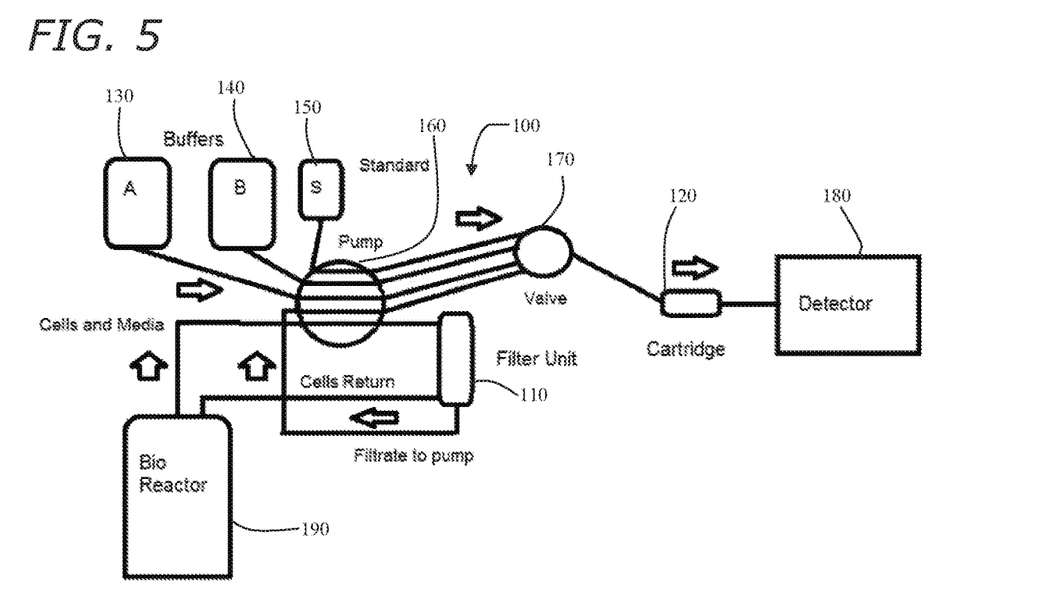
Figure 6:
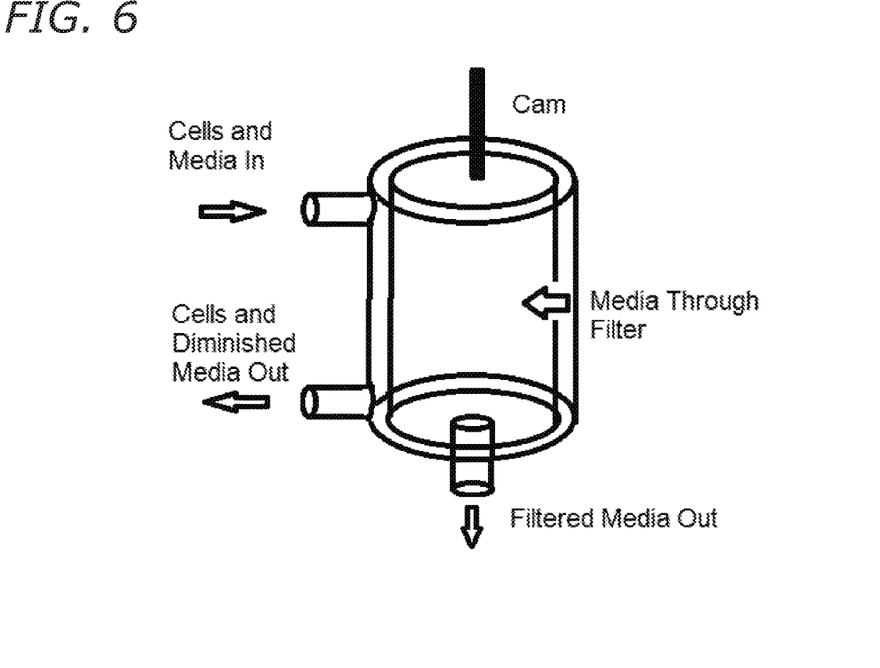
Figure 7:
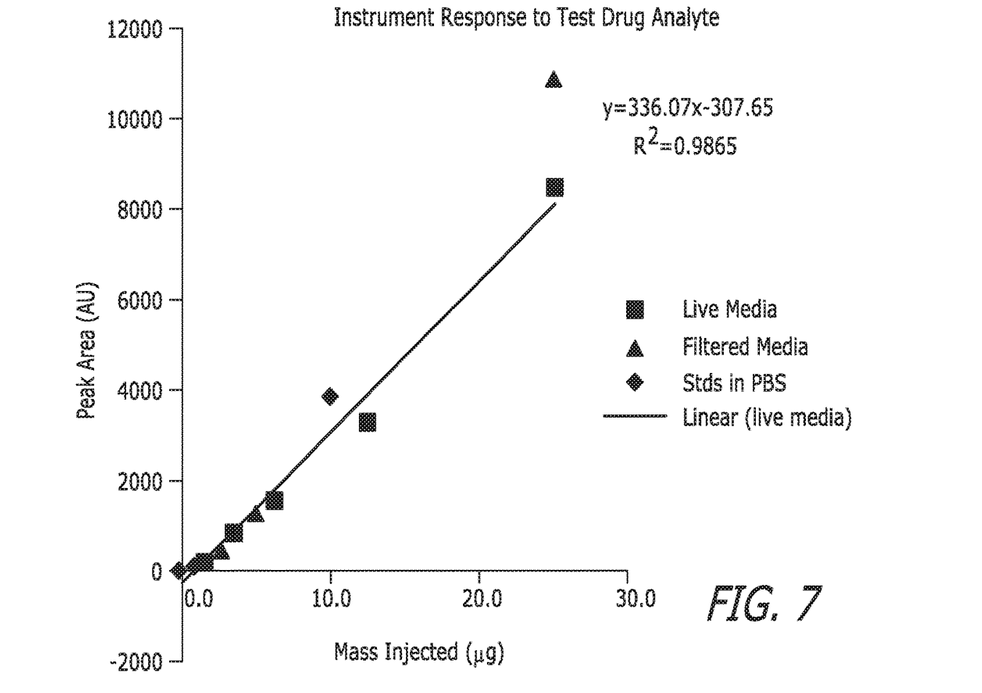
FIG. 7 shows the instrument response to test drug analyte, graphing peak area with respect to the mass injected. The overlapping response of analyte in media, filtered media or in a standard buffer solution demonstrates that the instrument gives the equivalent response with no interference from sample components.
Figure 8:
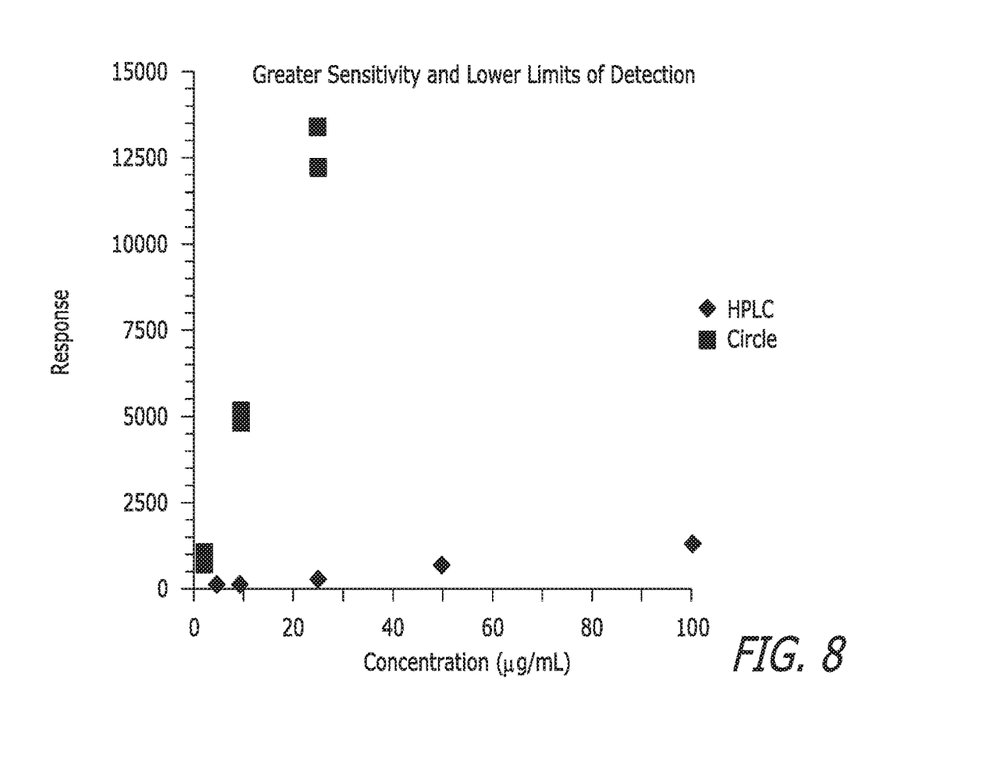
FIG. 8 shows the greater sensitivity and lower limits of detection of disclosed embodiments Circle Technology instrument when compared to a traditional laboratory test instrument like an HPLC. The lower detection limits allow measurement of the drug or analyte of interest sooner in the batch when compared to a laboratory HPLC.
Figure 9:
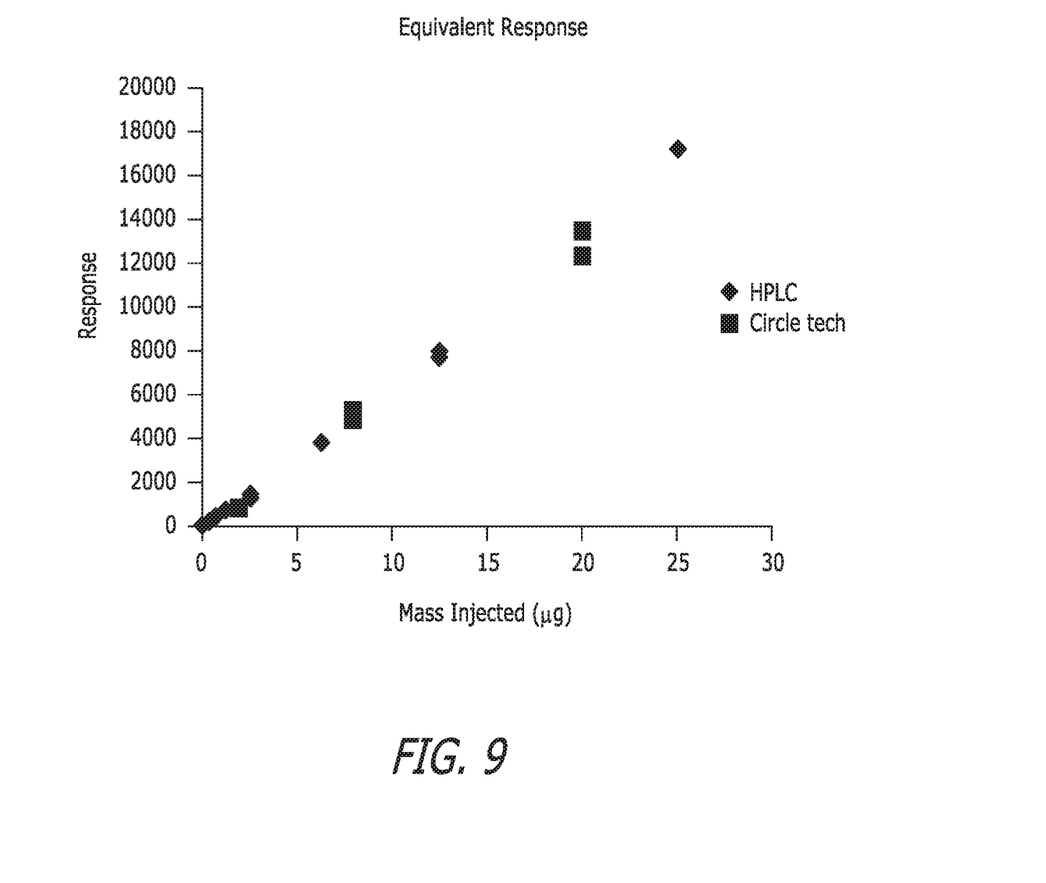
FIG. 9 shows that when the data from FIG. 8 is converted to response vs. mass injected, disclosed embodiments provide equivalent responses as compared to traditional laboratory HPLC, however disclosed embodiments provide these results much faster than traditional systems. "Circle Tech" refers to data produced by a system disclosed herein.

Common process analyzers include temperature, pH and dissolved oxygen sensing probes that are sterilized and placed in the reactor at the start of the cell/organism growth process or fermentation. However, for Process Analytical Technology (PAT), the amount of biologic or drug being produced as well as nutrients and nutrient metabolytes are often the most desirable measurement. Devices capable of maintaining sterility and quantifying the drug and/or analytes of interest as the fermentation progresses are limited in that they can often only measure the drug near the end of the batch when the concentrations are high. Disclosed herein are systems and devices that can measure analyte concentrations from beginning to end of the process. In certain embodiments the device can measure metabolites (e.g., wastes) for example, ammonia, and glutamic acid or the like.

In embodiments these measurements can inform process control by maintaining optimum production parameters. For example, systems disclosed herein can measure, monitor and adjust system pH, temperature, dissolved oxygen ($O_2$) content, media levels, media content including nutrient levels, amino acids, metabolite levels, etc., based on real-time analysis.

Many of the laboratory analytical tests for protein drugs are not amenable to real-time monitoring of the production of biologics. For example, the most common technique for measuring protein concentration uses ultraviolet spectroscopy to measure the absorbance at a wavelength of 280 nm. The test, usually called $A_{280}$, requires the pure drug in the presence of a non-interfering, i.e. non-absorbing buffer species. In a typical bioreactor there are various chemicals introduced in the fermentation media, e.g., free amino acids, vitamins and other chemicals that can interfere with a UV assay for proteins. To create a real time analyzer for the drug product, the test must be selective for the drug in the presence of the media.

Ligand binding assays have been used as a selective assay for proteins from fermentations. Usually antigens are bound to the bottom of well plates. Then the drugs are bound to well plates. Wash steps are involved to remove interfering species. The tests have the advantage of measuring a wide range of concentrations. However, the tests are labor and automation intensive. Due to long incubation times, the tests would not be amenable to measure a drug directly from fermentation in real time. Surface Plasmon Resonance (SPR) devices can sense proteins that are bound to a ligand surface. However, the dynamic range of an in situ SPR device for bioreactors is limited by the amount of protein on the surface. If the protein binding on the surface of the SPR device is permanent, as the fermentation progresses, the ligand surface becomes saturated with protein and no longer responds to changes in drug concentration in the media. Therefore the ideal real-time protein concentration measurements in a bioreactor will be accurate over a wide dynamic range, at all points of the fermentation.

Embodiments disclosed herein also include techniques whereby a biologic or protein of interest is "tagged" with an identifiable molecule such as, for example, a fluorescent marker or dye.

Embodiments include systems and devices that draw a sample solution from a bioreactor or fermentation vessel and automatically filters it to remove cellular material and other solids from the solution. Embodiments disclosed herein provide an instrument that measures the concentration of the biologic. Embodiments disclosed herein use real-time correction that quantitates the biologic in the presence of a changing "background" conditions due to changing buffer or fermentation conditions. The proteins in the filtrate solution are loaded onto means for isolating the biologic of interest, such as affinity media. The media preferentially binds the biologic over the other proteins and chemicals in the fermentation media. The media is washed to remove other chemicals and proteins. Embodiments disclosed herein can measure the concentration of biologics after being eluted from the means for isolating the biologic. Embodiments disclosed herein can measure the concentration of active biologics with sufficiently low limits of detection without derivatization and/or denaturing the sample, and minimizing the need for offline ligand binding assays.

Disclosed embodiments provide for measuring and then recovering intact, unadulterated and pure proteins or other biologics. This can be a source of material for other assays such as Mass Spectrometry or Ligand Binding assays. In particular the ligand binding assays are used to show how much protein is in its active form, as they involve the drug binding to a substrate. Disclosed embodiments also measure the functional biologics, as in certain embodiments misfolded proteins will not bind to the affinity media or other means for isolating the protein.

"Absorbance" as used herein can be calculated by $A=-\log(I/I_0)$, where $I_0$, can be the incident light beam intensity prior to introduction of the absorbing chemical, and I, can be the light intensity after the chemical is introduced.

"Absorbance spectrum" as used herein can be used to determine the wavelength of light at which absorbance is greatest.

"Affinity chromatography" as used herein is a method of separating biologics from a mixed sample. Affinity chromatography consists of first preparing the stationary phase by immobilizing one of the two recognized components on an insoluble hydrophobic polymer such as agarose. The sample is then applied to the stationary phase, which allows the analytes to bind to the stationary phase. The analyte or analytes are then washed and eluted.

"Analyte" as used herein refers to a chemical constituent that is subject to analysis, such as a drug, antibody, peptides, any molecule of interest, protein, cells, polypeptides, glucose, lactate, cholesterol, fructose, citrate, galactose, xylose, formate, proprionate, isocitrate, acetate, amino acids, etc. "Analyte" can mean more than a single type of analyte.

"Biologics" includes plant, animal, bacterial, and insect cells, as well as protein-based pharmaceuticals such as antibodies.

"Bioreactor" or "fermentation vessel" as used herein refers to a device that is used to grow cells or tissues, and used to support a biologically active environment.

"Filtrate" refers to media solution from which cellular debris and other non-analyte material has been removed by any means.

"Flow Cell" as used herein describes the flow through a container that contains the liquid while making a quantitative chemical measurement of the analytes of interest.

"Growth media" as used herein refers to a liquid that is designed to support the growth of microorganisms or cells.

"Modified version of Lambert-Beer Law" as used herein calculates the concentration $A_c = A_{280} - A_{320} = \varepsilon bc$, where $A_c$ is the corrected absorbance. Most proteins do not have chemical bonds that absorb the energy at 320 nm. However, if there are decreases in the transmitted light due to refractive index effects, then the decrease is observed as an apparent absorbance at 320 nm. Essentially the $A_{320}$ is a quantitation of the non-absorbance effects. Subtracting $A_{320}$ from $A_{280}$ gives a better estimation of the true absorbance due to the protein at 280 nm.

"Optical Absorbance" as used herein has been described by the Lambert-Beer Law $A = \varepsilon bc$, where c can be the concentration of the analyte or other chemical of interest, b can be the optical path length of the instrument, and $\varepsilon$ can be the extinction coefficient of the analyte at a specific wavelength. During absorbance, when a chemical is placed in the optical path, the chemical bonds in the analyte absorb the energy of the specific wavelength of light. The result can be a decreased in the amount of light reaching the photodetector.

"Optical Beams" as used herein refers to the light rays entering the flow cell were the buffer is refracted according to Snell's Law.

"Peristaltic Pump" as used herein can be an independent multichannel pump or multiple pumps that gradually administers measureable amounts of media into the system, as well as wash and elution buffers. "Peristaltic pump" can include independent channel peristaltic pumps.

"Photodetector" as used herein refers to a device that detects light. Photodetector can be suitable for some range of optical powers and can be sensitive in a given spectral region (range of optical wavelengths).

"Process Analytical Technology" as used herein provides monitoring and control of critical processes that provide characteristics of the cell population and control and optimization the fermentation process.

"Refractive Index Effects" as used herein refers to responses that the absorbance detector generates that are not due to absorbing chemicals but are due to changes in the buffer, like concentration of dissolved non-absorbing species or temperature. Often the Refractive Index effects determine the detection limit of the instrument, not the light source and electronics.

"Snell's Law" as used herein demonstrates that the angle of refraction in the flow cell will change with the new buffer. Snell's law is represented by the equation $n_1 \sin \Theta_1 = n_2 \sin \Theta_2$, where $n_1$ and $n_2$ can be the refractive indices of the two adjacent media, $\Theta_1$ can be the angle of incidence to normal, and $\Theta_2$ can be the angle of refraction. For a flow cell, $n_1$ can be the ambient air and $n_2$ can be the refractive index of the aqueous buffer. The change in refraction can be observed as a decrease in the transmitted light through the flow cell. The transmitted light intensity, I, can be less than the initial light intensity $I_0$, and can appear as an absorbance. This refractive index based signal can be independent of the analyte concentration and can be seen when buffers are switched with no analyte is present in the instrument.

"Sampling System" as used herein is any device or system for sterilely taking samples.

Systems for Determining Biologic Concentration

Embodiments disclosed herein include systems for determining a characteristic of a biologic or a bioprocess media. These characteristics can include, for example, the concentration or activity of the biologic or the temperature or pH of the growth media or nutrients and metabolites in the growth media or biologic.

Embodiments of the system can comprise a growth or fermentation vessel. A growth vessel described herein can comprise a bioreactor. Certain embodiments disclosed herein can use single-use bioreactors, autoclavable bioreactors, sterilizable-in-place bioreactors, batch bioreactors, sequence bioreactors, continuously stirred tanks, anaerobic contact processes, anaerobic filters, or the like. In certain embodiments a growth vessel can comprise a fermentation vessel of an appropriate volume.

The growth vessel can be of any appropriate volume. For example, the vessel can have a volume of less than 1 L, more than 1 L, more than 10 L, more than 100 L, more than 1000 L, more than 10,000 L, or the like.

In embodiments the system can comprise multiple growth vessels. For example, the system can comprise 2, 3, 4, 5, 6, 7, 8, 9, 10, 20, 40, 80, 160, or more growth vessels. In embodiments the vessels can be of identical, or similar, or non-identical volumes.

Certain embodiments include growth vessels suitable for growing organisms such as yeast, bacteria, or the like, that can produce the biologic or analyte of interest. Such organisms can include recombinant organisms. For example, *e. coli* comprising an expression vector can be used as a production organism.

Certain embodiments include growth vessels suitable for growing mammalian cells, insect cells, tissues, or the like. For example, Chinese hamster ovary (CHO) cells can be used to produce biologics or analytes of interest.

In embodiments, bioprocess media can comprise growth media, buffers, and the like. In embodiments, growth media can comprise, for example, CD OptiCHO Media, Dulbecco's Modified Eagle Medium, RPMI 1640, or the like. In embodiments the growth media used in the system depends upon the cell type used.

Embodiments disclosed herein can comprise perfusion or continuous bioreactors where material can be harvested. When the material is harvested and fresh media is introduced, the concentration of the biologic may drop. Embodiments of the system can calculate and increase the volume of the sample load.

In embodiments the cells or microorganisms within the growth vessel can release the biologic of interest into the growth media. In embodiments the cells or microorganisms can be lysed or can self-lyse to release the analyte or protein or biologic of interest into the growth media. In embodiments lysis can be achieved with the use of enzymes such as lysozymes. In embodiments lysis can be achieved with mechanical techniques, such as sonication.

In embodiments the cells or microorganisms within the growth vessel comprise the biologic of interest.

Embodiments of the system can comprise devices for sampling the growth media and cells or analytes therein. In embodiments the sampling system comprises sterile tubing and sterile receptacles. In embodiments the sampling system comprises a pump.

In embodiments, buffers, media, and samples can be pumped by for example, an independent multichannel peristaltic pump, or multiple independent pumps. In embodiments the pumps described herein can comprise for example, syringe pumps, infusion/withdrawal syringe pumps, push-pull syringe pumps, reciprocating piston pumps, dual reciprocating piston pumps, peristaltic pumps, positive displacement pumps, reciprocating pumps, gear pumps, screw pumps, rotary vane pumps, lobe pumps, cassette pumps, tube pumps, process pumps, hygienic pumps, close-coupled pumps, or the like.

In an embodiment an independent multichannel peristaltic pump draws material from a bioreactor through sterile tubing. The material includes fermentation media, cells and/or the biologic of interest.

Disclosed embodiments of the system can comprise a filter or filter system, or the like, to remove materials other than the biologic of interest from the growth or fermentation media. For example, media comprising cells can be sterilely removed from the growth vessel and pumped into a sterile cylindrical filter and housing. In an embodiment the cells and media flow down the outside of the cylindrical filter. In embodiments the media with the biologics can pass through the pores of the filter. In embodiments the biologics or analytes of interest can be affected by gravity, causing them to collect at the bottom of the filter. In certain embodiments, the filter is operated under liquid pressure, such as with a pump.

In embodiments sterile peristaltic tubing, routed through a second pump or second input in a multichannel pump, can be used to pump the filtrate out of the bottom of the filter, through a valve, and onto one or more stationary phase cartridges. The pump can control the time, flow rate and volume of how much filter sample is loaded onto the stationary phase, which can control the mass of the biologic loaded onto the cartridge. The processor can be used to control the pump. Certain embodiments disclosed herein comprise stationary phases for isolating biologics or analytes including, for example, affinity chromatography, ion exchange chromatography, or size-exclusion chromatography, expanded bed adsorption chromatographic separation, or reversed-phase chromatography, two-dimensional chromatography, pyrolysis gas chromatography, fast protein chromatography, countercurrent chromatography, chiral chromatography, iso-electric focusing, ion mobility, capillary electrophoresis, or the like. The volume of the sample used for isolating the biologic can be recorded.

After isolating the biologic or analyte, a characteristic of the biologic or analyte can be determined. For example, the concentration can be determined by determining the amount in a known volume. This can be determined by determining the absorbance spectra of the sample using an optical detector. In certain embodiments the optical detector wavelength measurements consist of for example, near infrared (NIR), mid-infrared (Mid-IR), Raman, UV-Vs, or the like.

Certain embodiments of the system can comprise an optical detector. In embodiments the optical detector can be configured to measure the absorbance spectrum for example, more than 190 nm, more than 200 nm, more than 210 nm, more than 220 nm, more than 230 nm, more than 240 nm, more than 250 nm, more than 260 nm, more than 280 nm, more than 290 nm, more than 300 nm, more than 310 nm, more than 320 nm.

In certain embodiments the optical detector can be configured to measure the absorbance spectrum for example, less than 190 nm, less than 200 nm, less than 210 nm, less than 220 nm, less than 230 nm, less than 240 nm, less than 250 nm, less than 260 nm, less than 280 nm, less than 290 nm, less than 300 nm, less than 310 nm, less than 320 nm.

In embodiments the system can comprise a flow through absorbance analyte detector, which can use the corrected absorbance, $A_c$, calculated from the difference between the absorbance at a wavelength that the analyte absorbs (e.g. 280 nm), $A_{abs}$, and one that it does not absorb, $A_{ref}$, (e.g. 320 nm) $A_c = A_{abs} - A_{ref} = \varepsilon bc$.

In embodiments, $A_c$ can be displayed as a time dependent flow-through absorbance. The $A_{ref}$ reading is indicative of the non-absorbance effects that are caused by the changes in the refractive index of the solution when the buffers are changed. When no analytes are introduced, but the buffers are changed, the $A_c$, has a significantly smaller response to the change in buffer when compared to $A_{abs}$. The result is a significantly lower detection limit for the analyzer meaning that low analyte levels at the start of a fermentation batch can be easily detected. In embodiments the system can detect concentrations as low as 100 picograms per mL.

Embodiments of the system can provide a real-time analyte correction measurement that can correct for problems like an occasional bubble or other contaminants within the flow line.

Embodiments of the device can use real-time wavelength subtraction that can take into account changes in room temperature over days and weeks giving corrected absorbance of the analyte. In certain embodiments the real-time wavelength subtraction can take into account changes in room temperature taken for example, more than 1 day, more than 2 days, more than 3 days, more than 4 days, more than 5 days, more than 6 days, more than 1 week, more than 2 weeks, more than 3 weeks, more than 4 weeks, more than 5 weeks, more than 6 weeks, more than 7 weeks, more than 8 weeks, or the like.

In certain embodiments the real-time wavelength subtraction can take into account changes in room temperature taken for example, less than 1 day, less than 2 days, less than 3 days, less than 4 days, less than 5 days, less than 6 days, less than 1 week, less than 2 weeks, less than 3 weeks, less than 4 weeks, less than 5 weeks, less than 6 weeks, less than 7 weeks, less than 8 weeks, or the like.

In embodiments, a sample can be passed through the photodetector. The sample can then be moved to a collector that can collect and temporarily store the biologic in a buffer at refrigerated or frozen temperatures. In certain embodiments the material can be recovered and sent to a quality control (QC) laboratory for additional identification and confirmation tests.

Further aspects comprise analyte detection system wherein a solution can be injected into the stream to calibrate or check calibration.

In embodiments the device can use sterile prefilled containers, including bottles or syringes, of buffers. In certain embodiments the end user is not required to prepare buffers.

In embodiments, tubing used with the system can be, PEEK, polyvinyl chloride, silicone rubber, fluoropolymer, PharMed, PTFE, or the like.

In embodiments the system is fully automated and can run unattended for the entire process run. For example, in certain embodiments the system can run unattended for 30 minutes, 1 hour, 2 hours, 3 hours, 10 hours, 20 hours, 1 day, 2 days, 3 days, 4 days, 5 days, 6 days, 1 week, 2 weeks, 3 weeks, 4 weeks, 1 month, 2 months, 3 months 4 months, 5 months, 6 months, 7 months, 8 months, 9 months, 10 months, 11 months, 1 year, 2 years, 3 years, or the like.

In embodiments the system can have its detection limits set at 1 pg/mL, 10 pg/mL. 20 pg/mL, 30 pg/mL, 40 pg/mL, 50 pg/mL, 60 pg/mL, 70 pg/mL, 80 pg/mL, 90 pg/mL, 100 pg/mL, 110 pg/mL, 120 pg/mL, 130 pg/mL, 140 pg/mL, 150 pg/mL, 160 pg/mL, 170 pg/mL, 180 pg/mL, or the like.

In embodiments the device can measure a drug from start to finish of the batch. In certain embodiments the growth media nutrient and metabolite levels can be measured in real time. If certain levels drop too low, the cell growth will decrease.

In certain embodiments, the system can provide a user with data in less than one second after sampling, or less than ten seconds after sampling, less than 20 seconds after sampling, less than 30 seconds after sampling, less than 40 seconds after sampling, less than 50 seconds after sampling, less than one minute after sampling, less than two minutes after sampling, less than three minutes after sampling, less than four minutes after sampling, less than five minutes after sampling, less than six minutes after sampling, less than seven minutes after sampling, less than eight minutes after sampling, less than nine minutes after sampling, less than ten minutes after sampling, less than eleven minutes after sampling, less than twelve minutes after sampling, less than thirteen minutes after sampling, less than fourteen minutes after sampling, less than fifteen minutes after sampling, less than sixteen minutes after sampling, less than seventeen minutes after sampling, less than eighteen minutes after sampling, less than nineteen minutes after sampling, less than twenty minutes after sampling, less than twenty-one minutes after sampling, less than twenty-two minutes after sampling, less than twenty-three minutes after sampling, less than twenty-four minutes after sampling, less than twenty-five minutes after sampling, less than twenty-six minutes after sampling, less than twenty-seven minutes after sampling, less than twenty-eight minutes after sampling, less than twenty-nine minutes after sampling, less than thirty minutes after sampling, or the like.

In certain embodiments the device can have a single wavelength, or dual wavelength absorbance detector, or the like to remove or reduce the refractive index interferences.

In embodiments the device can store a purified sample at refrigerated or frozen temperatures.

In embodiments the device can be used for different types of analysis such as, for example, mass spectrometry, or ligand binding assays.

Embodiments disclosed herein can comprise means for storing data collected by the system. In embodiments, the data can be stored on for example, a hard drive, an optical drive, a cloud system, a thumb drive, an external hard drive, or the like. In embodiments the data can be propagated, such as via email or text message, to a recipient or recipient list.

Methods for Determining Characteristics of Biologics or Analytes

In embodiments, methods for determining characteristics of biologics or analytes disclosed herein can comprise growing cells or organisms, sampling the growth media, isolating the biologic or analyte of interest from the sample, and characterizing the biologic.

In embodiments, cells or organisms that produce or comprise the analyte or biologic of interest can be grown in a growth or fermentation vessel or bioreactor comprising an appropriate growth media.

In embodiments the cells or microorganisms can be allowed to grow or reproduce for a fixed period of time. For example, the cells or microorganisms can be allowed to grow for 1 day, 2 days, 3 days, 4 days, 5 days, 6 days, 7 days, 10 days, 14 days, 21 days, 28 days, 35 days, or more. In embodiments the cells or microorganisms can be allowed to grow or reproduce for not less than 1 day, not less than 2 days, not less than 3 days, not less than 4 days, not less than 5 days, not less than 6 days, not less than 7 days, not less than 10 days, not less than 14 days, not less than 21 days, not less than 28 days, not less than 35 days, or the like.

In embodiments the growth period can be determined by measuring parameters of the growth media, such as drug concentration, optical density, turbidity, pH, dissolved $O_2$, or the like. The growth period can be completed when a media parameter is reached, such as an optical density of 3.0.

Embodiments of the disclosed methods comprise sampling the growth media comprising the biologic or analyte of interest. In embodiments the sampling is performed sterilely. The sampling can be performed automatically under the control of a processor. For example, the sampling can be performed at predetermined time points, or when certain milestones are reached, or a combination thereof.

In embodiments the pump can load filtered analyte onto a stationary phase allowing purified samples to be drawn out of the stationary phase.

The sampling system can draw samples continuously or at discreet time intervals or based upon parameter "triggers." For example, the sampling system can draw samples every minute, two minutes, three minutes, four minutes, five minutes, six minutes, seven minutes, eight minutes, nine minutes, ten minutes, eleven minutes, twelve minutes, thirteen minutes, fourteen minutes, fifteen minutes, sixteen minutes, seventeen minutes, eighteen minutes, nineteen minutes, twenty minutes, twenty-one minutes, twenty-two minutes, twenty-three minutes, twenty-four minutes, twenty-five minutes, twenty-six minutes, twenty-seven minutes, twenty-eight minutes, twenty-nine minutes, thirty minutes, or the like.

In other embodiments, the sampling system can draw samples when the pH or optical cell density reaches a certain value, and thereafter at a fixed time interval. In embodiments the system can cease sample collection based on a time limit or when a fermentation parameter reaches a fixed value, such as for example, when the cell density reaches a certain value.

In embodiments the samples taken can be of any appropriate volume, such as 1 μL, more than 1 μL, more than 5 μL, more than 10 μL, more than 20 μL, more than 30 μL, more than 40 μL, more than 50 μL, more than 60 μL, more than 70 μL, more than 80 μL, more than 90 μL, more than 0.25 mL, more than 0.5 mL, more than 1 mL, more than 2 mL, more than 3 mL, more than 4 mL, more than 5 mL, more than 6 mL, more than 7 mL, more than 8 mL, more than 9 mL, more than 10 mL, more than 11 mL, more than 12 mL, more than 13 mL, more than 14 mL, more than 20 mL, more than 30 mL, more than 40 mL, more than 50 mL, more than 60 mL, more than 70 mL, or the like.

Certain embodiments disclosed herein comprise sample volumes ranging from for example, less than 1 μL, less than 5 μL, less than 10 μL, less than 20 μL, less than 30 μL, less than 40 μL, less than 50 μL, less than 60 μL, less than 70 μL, less than 80 μL, less than 90 μL, less than 0.25 mL, less than 0.5 mL, less than 1 mL, less than 2 mL, less than 3 mL, less than 4 mL, less than 5 mL, less than 6 mL, less than 7 mL, less than 8 mL, less than 9 mL, less than 10 mL, less than 11 mL, less than 12 mL, less than 13 mL, less than 14 mL, less than 15 mL, less than 20 mL, less than 30 mL, less than 40 mL, less than 50 mL, less than 60 mL, less than 70 mL, or the like. The sampling can be performed continuously.

In certain embodiments, the sampling system can take a large sample volume, and as concentration of the drug increases in the bioreactor, the device can calculate a new smaller sample volume. In other embodiments the device can calculate and increase the sample volume.

In certain embodiments, in perfusion bioreactors where some of the media is harvested, and fresh media is added, the system can increase the sample volume to compensate for the lower analyte concentration.

In certain embodiments the sampling system can filter the sample through a cylindrical filter. The filter can be made of a semi permeable membrane or nylon fibers or Teflon, or polycellulose or the like.

In certain embodiments the cylindrical filter can be rotated on a cam at high enough revolutions per minute to create centrifugal force in the filter. The centrifugal force drives the cells away from the surface of the filter, cleaning and extending the lifetime of the cylindrical filter. In embodiments the filter can rotate at any appropriate rate, such as, for example, over 100 RPM, over 200 RPM, over 400 RPM, over 800 RPM, over 1500 RPM, over 3000 RPM, over 5000 RPM, or more, or the like.

In embodiments that sampling system uses a calibration curve using a standard of known concentration based upon the mass injected, which is calculated from the volume injected times the concentration. In other embodiments, unknown samples are calculated from a plot of instrument response versus mass injected.

In embodiments, the sample comprising the biologic or analyte of interest is then filtered to remove cellular debris or other material that can interfere with characterization. For example, a cylindrical filter, a planar filter, or a tangential flow filter can be used. In certain embodiments the sterility of the cells are preserved and the cells can be returned to the bioreactor. In other embodiments the cells are pumped to a waste container. In embodiments of the methods disclosed herein, filtration can be followed by determining a characteristic of the biologic or analyte of interest.

Certain embodiments can comprise isolating the biologic of interest from the sample, which can comprise contacting the sample with an affinity media comprising an protein that the biologic binds to, for example an antibody or antigen; washing the media to remove unbound material; and eluting the biologic with an appropriate buffer.

Certain methods can comprise quantifying the biologic or analyte of interest, which can comprise measuring the concentration of the biologic by determining the protein concentration of the eluted biologic. For example, methods can comprise the use of affinity media to isolate the biologic or analyte of interest. Next, when removing bound proteins from the affinity media, a different buffer, usually with a lower pH, can be used to interrupt any bonding between the media and the proteins or analyte. The different buffer has a different chemical composition and/or concentration of solutes and therefore has a different refractive index. Snell's Law demonstrates that the angles of refraction at the optical detector will change with the new buffer. The change in refraction usually is observed as a decrease in the transmitted light through the flow cell. The transmitted light intensity, I, is usually less than the initial light intensity $I_0$ and is calculated by the instrument as an absorbance. This refractive index based signal is independent of the drug concentration and can be seen when buffers are switched with no analyte e.g. biologic present on the media, and gives a false apparent absorbance reading for a flow-through absorbance measurement. Accurate quantitation can only occur when the absorbance due to the analyte is much larger than the apparent absorbance due to the buffer refractive index change. In general for most flow through absorbance detectors used for affinity chromatography and other methods, the refractive index effects determine the detection limit of the instrument, not the noise levels on the light source and electronics. In a bioreactor, the drug concentrations are low at the start of the fermentation; in embodiments the analyzer uses an optical detector that does not respond to buffer changes and gives significantly low limits of detection limits.

In laboratory testing for proteins, there have been applications of quantifying proteins using a second wavelength to correct for non-absorbance optical effects. A typical laboratory UV protein analysis involves putting the sample in a quartz cuvette and measuring the absorbance at 215 nm and 320 nm. A modified version of the Lambert-Beer Law is used to calculate the concentration.

$$A_c = A_{215} - A_{320} = \varepsilon bc$$

Where $A_c$ is the corrected absorbance. Most proteins do not have chemical bonds that absorb the energy at 320 nm. However, if there are decreases in the transmitted light due to non-absorbance effects like refractive index changes or light scattering, then the decrease is observed as an apparent absorbance at 320 nm. Essentially the $A_{320}$ is a quantitation of the non-absorbance effects. Subtracting $A_{320}$ from $A_{215}$ gives a better estimation of the true absorbance due to the protein at 215 nm.

In certain embodiments the device can have a flow through absorbance detector that uses the corrected absorbance, $A_c$, calculated from the difference between the absorbance at a wavelength that the drug protein absorbs (e.g. 215 nm), $A_{abs}$, and one that it does not absorb, $A_{ref}$ (e.g. 320 nm)

$$A_c = A_{abs} - A_{ref} = \varepsilon bc$$

The device can be set to wavelengths for $A_{abs}$ and $A_{ref}$ to maximize sensitivity based upon the drug's inherent absorbance spectrum, not necessarily 215 and 320 nm. For this device, $A_c$ can be displayed as a time dependent flow-through absorbance. The $A_{ref}$ reading is indicative of the non-absorbance effects that are caused by the changes in the refractive index of the solution when the buffers are changed. When no protein is introduced but the buffers are changed, the $A_c$ has a significantly smaller response to the change in buffer when compared to $A_{abs}$. The result is a significantly lower detection limit for the analyzer meaning that low drug levels at the start of a fermentation batch can be easily detected.

Some flow through detection devices take a blank reading with a changing buffer but no analytes present and subtract this from subsequent runs. However, the corrected absorbance, $A_c$ is better than making a blank subtraction because run-to-run imprecision in timing and flow rates can confound the baseline subtraction. Embodiments provide a real time subtraction that can correct for other problems like the occasional bubble in the flow line. Also, solution refractive index is also a function of temperature. Changes in the room temperature over days and weeks render inaccuracies in a blank subtraction. Therefore, this real-time wavelength subtraction is more accurate when temperatures change over days or weeks like in a manufacturing environment.

For example, embodiments comprise a method for determining the concentration of an analyte based on the calibration of the analyte or analytes response and the known volume of media loaded on the affinity media. In certain embodiments, as analyte concentration increases within the fermentation bioreactor over time, the said computing method will calculate a smaller sample volume to load.

Embodiments comprise a method to effectively expand the range of sample concentrations that the instrument can measure to those far beyond current practice. For example, with affinity chromatography, essentially 100% of the analytes that come in contact with the stationary phase are bound to it. This allows for sample pre-concentration, i.e, large volumes of sample can be loaded onto an affinity cartridge to focus the analytes into the smaller cartridge volume. Unlike traditional HPLC methods with fixed sample injection volumes, this instrument can vary the volume of sample that is loaded. The flow rate and loading time of the sample solution onto the stationary phase is precisely controlled for accurate quantitation. The mass of analyte loaded on the beads, M, can be described by: $M=C_s Ft$, where $C_s$ is the concentration of the analyte in the sample (usually in µg/µL), F is the volumetric flow rate over the beads (usually in µL/min), and t is the load time in minutes. The average concentration of analyte, $C_d$, at the detector can be determined from the instrument's calibration response. Because the mass of drug seen at the detector is equal to the mass of drug loaded onto the beads, the following equation holds true $M=C_d V_a$ where M is the mass loaded onto (and removed from) the beads, and $V_a$ is the volume of the analyte as measured by the detected peak volume passing through the detector. In practice the concentration at the detector must be above the limit of detection of the device. However the load volume can be increase to pre-concentrate enough mass onto the stationary phase cartridge in order to be measurable at the detector.

Embodiments comprise a method for computing the mass of analyte that should be loaded to allow sufficient material to reach the flow-through detector. In addition, the mass is computed to prevent excessive material from reaching the cartridge and/or flow-through detector. For example, at the start of the growth process, when the analyte concentrations are low, the mass of analyte loaded is calculated to exceed the Mass Lower Limit of Quantitation of the detector $M_L$ (usually in µg). As the concentration of the analyte in the media increases, the device automatically decreases the mass loaded to prevent over-loading of the stationary phase with analytes and/or analyzing above the Mass Upper Limit of Quantitation of the detector, $M_U$ (usually in µg). The mass loaded can be controlled by varying the flow rate and/or loading time of the sample solution onto the stationary phase. The instrument's calibration is used to calculate $C_s$ for a sample. In certain embodiments the sample loading flow rate is held fixed and the load time is varied. Solving for time, $t=M/C_s F$. The instrument calculates the load time such that the mass loaded $M_U>M>M_L$. At the start of the growth process ab initio information is used to determine a starting $C_s$. As $C_s$ increases, the load time is decreased to shorten the total analysis time. In other embodiments, the flow rate can be varied, e.g. $F=M/C_s t$. with the same boundaries on M.

In certain embodiments the load time can be for example, more than one second, more than ten seconds, more than 20 seconds, more than 30 seconds, more than 40 seconds, more than 50 seconds, more than one minute, more than two minutes, more than three minutes, more than four minutes, more than five minutes, more than six minutes, more than seven minutes, more than eight minutes, more than nine minutes, more than ten minutes, more than eleven minutes, more than twelve minutes, more than thirteen minutes, more than fourteen minutes, more than fifteen minutes, more than sixteen minutes, more than seventeen minutes, more than eighteen minutes, more than nineteen minutes, more than twenty minutes, more than twenty-one minutes, more than twenty-two minutes, more than twenty-three minutes, more than twenty-four minutes, more than twenty-five minutes, more than twenty-six minutes, more than twenty-seven minutes, more than twenty-eight minutes, more than twenty-nine minutes, more than thirty minutes, or the like.

In certain embodiments the load time is for example, less than one second, less than ten seconds, less than 20 seconds, less than 30 seconds, less than 40 seconds, less than 50 seconds, less than one minute, less than two minutes, less than three minutes, less than four minutes, less than five minutes, less than six minutes, less than seven minutes, less than eight minutes, less than nine minutes, less than ten minutes, less than eleven minutes, less than twelve minutes, less than thirteen minutes, less than fourteen minutes, less than fifteen minutes, less than sixteen minutes, less than seventeen minutes, less than eighteen minutes, less than nineteen minutes, less than twenty minutes, less than twenty-one minutes, less than twenty-two minutes, less than twenty-three minutes, less than twenty-four minutes, less than twenty-five minutes, less than twenty-six minutes, less than twenty-seven minutes, less than twenty-eight minutes, less than twenty-nine minutes, less than thirty minutes, or the like.

In disclosed embodiments the pump or pumps can be set to control the time, flow rate, and volume of the filtered sample that is loaded onto the stationary phase, thus allowing the user to control the mass of the biologics loaded onto the cartridge. This is different from traditional practice in HPLC where for a given method the flow rate and time and sample volume is always the same during loading.

In embodiments, a method for changing the load volume during operation can include the ability to load higher sample volumes, such as for example, not more than 1 µL, not more than 5 µL, not more than 100 µL, not more than 250 µL, not more than 500 µL, not more than 750 µL, not more than 1 mL, not more than 2 mL, not more than 3 mL, not more than 4 mL, not more than 5 mL, not more than 6 mL, not more than 7 mL, not more than 8 mL, not more than 9 mL, not more than 10 mL, not more than 11 mL, not more than 12 mL, not more than 13 mL, not more than 14 mL, not more than 15 mL, or the like. In embodiments, the load volume can be pushed during operation such as for example, 1 µL, not less than 5 µL, not less than 100 µL, not less than 250 µL, not less than 500 µL, not less than 750 µL, not less than 1 mL, not less than 2 mL, not less than 3 mL, not less than 4 mL, not less than 5 mL, not less than 6 mL, not less than 7 mL, not less than 8 mL, not less than 9 mL, not less than 10 mL, not less than 11 mL, not less than 12 mL, not less than 13 mL, not less than 14 mL, not less than 15 mL, or the like.

In embodiments, the method can include real-time feedback data to a process controller processor which can automatically maintain growth media conditions, such as for example, volume, temperature, pH, dissolved $O_2$, nutrient levels such as, for example, amino acids, waste levels, and the like. In embodiments the system can provide these data every 2 minutes, every 5 minutes, every 10 minutes, every 20 minutes, every 30 minutes, every hour, every 2 hours, every 3 hours, every 5 hours, every 8 hours, or the like.

In certain embodiments, the method can provide a user with data in less than one second after sampling, or less than ten seconds after sampling, less than 20 seconds after sampling, less than 30 seconds after sampling, less than 40 seconds after sampling, less than 50 seconds after sampling, less than one minute after sampling, less than two minutes after sampling, less than three minutes after sampling, less than four minutes after sampling, less than five minutes after sampling, less than six minutes after sampling, less than seven minutes after sampling, less than eight minutes after sampling, less than nine minutes after sampling, less than ten minutes after sampling, less than eleven minutes after sampling, less than twelve minutes after sampling, less than thirteen minutes after sampling, less than fourteen minutes after sampling, less than fifteen minutes after sampling, less than sixteen minutes after sampling, less than seventeen minutes after sampling, less than eighteen minutes after sampling, less than nineteen minutes after sampling, less than twenty minutes after sampling, less than twenty-one minutes after sampling, less than twenty-two minutes after sampling, less than twenty-three minutes after sampling, less than twenty-four minutes after sampling, less than twenty-five minutes after sampling, less than twenty-six minutes after sampling, less than twenty-seven minutes after sampling, less than twenty-eight minutes after sampling, less than twenty-nine minutes after sampling, less than thirty minutes after sampling, or the like.

Embodiments include a method for notifying an operator or engineer when the results are out of specification. The notification can be via email, text, telephone call, push notifications, or a combination thereof, or the like. Embodiments include a method for notifying an operator or engineer at certain time intervals, for example, every 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes or the like, 2 hours, 4 hours, 8 hours, or the like. These time intervals can be varied depending upon process parameters. For example, the frequency of notifications can increase when cell growth enters log phase, or if cell waste products increase over a threshold value.

Embodiments include a method for returning cells back to the bioreactor in a sterile form. Certain embodiments include methods for mounting the device to other locations such as, for example, filtration, centrifugation, purification, UF/DF (buffer exchange), formulation, or the like.

Certain embodiments include methods for monitoring other types of chemistries such as, for example, reverse phase and ion exchange cartridges to measure additives in electroplating baths, nitrates and other waste build up in aquaculture tanks (salmon, shrimp, oysters, crabs, lobsters, or the like), traditional small molecule drug manufacturing, liquid phase chemical manufacturing, surfactants, leeching metals in gold or platinum manufacturing, soft drinks (flavor, coloring, and caffeine), decaffeination of coffee, or the like.

Certain embodiments include methods for storing purified drug and/or samples at refrigerated and/or frozen temperatures. The refrigerated and or frozen samples could serve as a source of purified material for use in other more elaborate laboratory tests like ligand binding assays, mass spectrometry or the like.

Certain embodiments include methods in which only the correctly folded, biologically active form of the drug is measured. In these embodiments, misfolded monoclonal antibodies, misfolded proteins or the like, are excluded from binding to the affinity stationary phase and are washed away with the other media components.

Embodiments can comprise pre-concentrating samples with low analyte concentrations such that the mass loaded onto the stationary phase, for example an affinity cartridge exceeds the Lower Limit of Quantitation of the detection system; this effectively lowers the concentration limits of detection of the instrument Embodiments can include calculating smaller load volumes as the concentration of analytes increases in the bioreactor to prevent exceeding the Upper Limit of Quantitation of the detection system.

Embodiments include employing a non absorbing reference wavelength to significantly reduce or remove non-absorbance refractive index effects that occur when changing buffers in affinity chromatography methods.

Embodiments include methods of correcting for buffer background refractive index effects thus allowing the measurement of far lower analyte concentrations;

Embodiments include a method for calculating the sample load volume to ensure that the mass of drug loaded is within between the lower and upper limits of quantitation of the detection system.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present disclosure, which is defined solely by the claims. Accordingly, embodiments of the present disclosure are not limited to those precisely as shown and described.

Certain embodiments are described herein, including the best mode known to the inventors for carrying out the methods and devices described herein. Of course, variations on these described embodiments will become apparent to those of ordinary skill in the art upon reading the foregoing description. Accordingly, this disclosure includes all modifications and equivalents of the subject matter recited in the claims appended hereto as permitted by applicable law. Moreover, any combination of the above-described embodiments in all possible variations thereof is encompassed by the disclosure unless otherwise indicated herein or otherwise clearly contradicted by context.

Groupings of alternative embodiments, elements, or steps of the present disclosure are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the disclosure are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the," and similar referents used in the context of describing the disclosed embodiments (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present disclosure and does not pose a limitation on the scope of the embodiments otherwise claimed. No language in the present specification should be construed as indicating any non-claimed element essential to the practice of the disclosed embodiments.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present disclosure so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the disclosed embodiments. These publications are provided solely for their disclosure prior to the filing date of the present application. All statements as to the date or representation as to the contents of these documents is based on the information available to the applicant and does not constitute any admission as to the correctness of the dates or contents of these documents.

EXAMPLES

The following non-limiting examples are provided for illustrative purposes only in order to facilitate a more complete understanding of representative embodiments. These examples should be construed to limit any of the embodiments described in the present specification, including those pertaining to the methods of giving real-time analyte concentration measurements in fermentation bioreactors.

Example 1

Real-time Concentration Measurement of Biologics

A bioreactor is seeded with mammalian cells expressing a biologic of interest. Samples are continuously drawn from the fermentation reactor but the reactor maintains sterility because no material can re-enter the fermenter. The sample solution is filtered to remove cellular material then the filtrate is passed over affinity media with an antibody designed to bind to the biologic. Under load conditions, the biologic binds to the affinity media. Depending upon the time of the fermentation, the volume of sample passing over the affinity media can be varied. For example, early in the fermentation, when drug concentrations are small, a sufficient volume of sample material can be washed over the affinity media to load the media with enough drug mass to be quantitated at the detector. When the fermentation has progressed for some time and the drug concentrations are larger, less volume of media is washed over the affinity stationary phase. This prevents total saturation of the stationary phase by the protein. The time and volume of loading is controlled to calculate of the concentration of drug in the loaded sample. The scale of sample volumes is in the µL to mL range so the volume of sample removed from the reactor is insignificant.

When loading is complete, a new wash solution flows over the affinity stationary phase to remove all other fermentation media components. The wash leaves behind only the biologic bound to the affinity stationary phase. Then the buffer solution is changed to a solution that removes the biologic from the affinity stationary phase. The biologic is released from the stationary phase and flows into an optical detector. The detector senses the concentration of drug as it is removed from the stationary phase.

Many flow-through optical absorbance detectors have difficulty measuring a protein or other chemical when the background buffer conditions are rapidly changing. Ideally a flow-through absorbance detector would only respond to the protein drug. However, most flow-through absorbance detectors create an interfering signal when the buffer changes, due to the change in refractive index of the buffer.

Example 2

Real-time Measurement of Analytes

Fermentation media is drawn from a bioreactor fermenting e. co/i. The media is filtered with filtration. The filtered solution is loaded onto a cartridge with an affinity chromatography stationary phase. The *e coli* cells produce a protein of interest that preferentially binds to the stationary phase while others pass through the cartridge into a waste receptacle. A wash buffer removes any non-bound proteins. A low pH elution buffer removes the protein of interest from the beads and passes it on to an analyte detector. The analyte detector signal is proportional to the protein concentration and does not respond to the buffer. The detector has real time non-absorbing wavelength subtraction to correct for the changing buffer background. The proteins of interest are collected in a refrigerated collector which can become a source of pure material for Quality Control Laboratory analyses.

A microprocessor calculates the concentration of the protein based on the calibration of the protein response and the known volume of material loaded onto the cartridge. As the protein concentration increases in the bioreactor over time, the microprocessor will calculate a smaller sample volume to load.

Example 3

Real-time Measurement of Vaccine Production

Media is drawn from a bioreactor fermenting insect cells that are producing viral proteins for use in a vaccine. The media containing the protein is filtered with a sampling system. The filtered solution is loaded onto a cartridge with an affinity chromatography stationary phase. The protein preferentially binds to the media while others pass through the cartridge into a waste receptacle. A wash buffer removes any non-bound proteins. A low pH elution buffer removes the protein of interest from the stationary phase and passes it on to an analyte detector. The analyte detector signal is proportional to the protein concentration and does not respond to the buffer. The detector has real time non-absorbing wavelength subtraction to correct for the changing buffer background. The proteins of interest are collected in a refrigerated collector which can become a source of pure material for Quality Control Laboratory analyses.

A microprocessor calculates the concentration of the protein based on the calibration of the protein's response and the known volume of material loaded onto the cartridge. As the protein concentration increases in the bioreactor over time, the microprocessor will calculate a smaller sample volume to load.

Example 4

Real-time Measurement of Analytes

Media is drawn from a bioreactor fermenting yeast cells. The media is filtered with a sampling system. The filtered solution moves loaded onto a cartridge with an affinity chromatography stationary phase. The yeast cells produce a protein of interest that preferentially binds to the media while others pass through the cartridge into a waste receptacle. A wash buffer removes any non-bound proteins. A low pH elution buffer removes the protein of interest from the beads and passes it on to an analyte detector. The analyte detector signal is proportional to the protein concentration and does not respond to the buffer. The detector has real time non-absorbing wavelength subtraction to correct for the changing buffer background. The proteins of interest are collected in a refrigerated collector which can become a source of pure material for Quality Control Laboratory analyses.

A microprocessor calculates the concentration of the protein based on the calibration of the protein response and the known volume of material loaded onto the cartridge. As the protein concentration increases in the bioreactor over time, the microprocessor will also calculate a smaller sample volume to load.

Example 5

Device Operation

Cells and media are pumped from the Bioreactor 190 with a multichannel pump 160. The cells and media are pumped into the top of a cylindrical filter unit 110. Inside the filter unit is a cylindrical membrane filter. The cells cannot pass through the membrane, but the fermentation media and drug can. The cells can be returned to the bioreactor or can be pumped to waste. The filtrate containing media and drug is pumped to a valve and then onto a cartridge 120. The filtrate passes over the stationary phase of the cartridge. The drugs bind to the stationary phase and the media does not. The valve 170 is turned and Buffer A 130, pH 7.2 is pumped over the cartridge to release the drug. The valve is turned and Buffer B 140, pH 3.0 is pumped over the cartridge to release the drug. The drug is measured by an optical detector 180. The valve is turned to Buffer A again to regenerate the cartridge back to pH 7.2. For calibration, the valve is turned to pump a Standard Solution 150 of a known drug concentration. The standard is process just like the samples. The standard solution can be measured multiple times with varying load volumes to generate a calibration curve. The detector responses from samples are compared to the calibration curve to determine the concentration of drug in the bioreactor sample.

Sample liquid from the bioreactor containing cells, fermentation media and drug is pumped into a plastic filter unit. The filter unit and connecting tubing lines are self-contained and have been manufactured to ensure sterility (either by heat (autoclaving) or irradiation (gamma rays)). The filter housing is a cylindrical container that has a concentric cylindrical membrane filter inside. There is a small gap between the inner housing wall and the outer diameter of the membrane filter. As the sample is pumped into the unit, it passes down the filter along the gap. The pump pressure forces the fermentation media and drug through the pores of the membrane filter. The cells are too big to pass through the membrane. The cells which now have a diminished volume of the fermentation media, pass along the outside of the membrane filter and out a port at the bottom. In some configurations when cells and media must be conserved, the cells can be pumped back into the bioreactor. In other configurations the cells are pumped to a waste container. The filtrate containing media and the drug collect in the bottom of the inside of the membrane cylinder. The filtrate can be pumped through a sealed port with outlet tubing at the bottom of the filter. In certain embodiments, the internal membrane cylinder can be rotated on a cam, at 3600 revolutions per minute. The rotation provides centrifugal force in the gap between the membrane filter and filter housing. The centrifugal force spins the sample. The heavier cells are forced to the inner wall of the housing away from the surface of the membrane filter. The force serves to keep the filter clean, thus extending the membrane lifetime.

Example 6

Real-time Measurement of Growth Media Parameters

Media is drawn from a bioreactor fermenting yeast cells using a reciprocating piston pump. The media is analyzed to measure various characteristics including pH, dissolved $O_2$, temperature, amino acid concentration, and amino acid metabolite concentration. These data are collected and compared by a processor to determine if the values are within process parameters and if not, what steps are to be taken. When the nutrient and amino acid levels in the bioreactor fall below the specified range for optimal cell growth, fresh media is added to the bioreactor to increase the levels to the acceptable range. The nutrient and amino acids values are thus maintained automatically. Similarly, pH and dissolved oxygen levels are maintained within a desired range; if a test value is not inside the desired range, the proper corrective measure is taken automatically while an "alert" email is sent to a technician.

The invention claimed is:

1. A system for determining real-time analyte concentration measurements from fermentation liquid inside a growth vessel, comprising: a growth vessel comprising a fermentation liquid; a sampling system; a filtration system comprising a filter rotating at 3600 RPM; a cartridge with a stationary phase; an analyte detection system; a fraction collector; and a microprocessor, wherein said analyte concentration is less than 10 ug/mL.

2. The system of claim 1, further comprising a sterile prefilled solvent reservoir.

3. The system of claim 1, further comprising a pumping system.

4. The system of claim 1, further comprising a multiport valve.

5. The system of claim 1, further comprising prefilled solvent reservoirs.

6. The system of claim 1, further comprising an optical detector.

7. The system of claim 1, wherein said sampling system comprises a multichannel pump.

8. The system of claim 1, wherein said analyte comprises a biologic.

9. The system of claim 1, wherein said analyte comprises a drug.

10. The system of claim 1, wherein said analyte comprises an antibody.

11. The system of claim 1, wherein said analyte comprises a peptide.

12. A method for determining real-time analyte concentration measurements from fermentation liquid inside a growth vessel, comprising:
   providing the system for determining real-time analyte concentration measurements of claim 1;
   producing an analyte in the growth vessel comprising the fermentation media;
   sampling and filtering the analyte in the sampling system and the filtration system, respectively;
   loading the analyte onto the cartridge with the stationary phase; and
   determining the concentration of analyte with the analyte detection system.

13. The method of claim 12, wherein a solution of known concentration is injected into the sampling system to calibrate or check calibration of said sampling system.

14. The method of claim 12, further comprising measuring data values for parameters including pH, dissolved $O_2$, temperature, amino acid concentration and amino acid metabolite concentration; transmitting the measured data values to a processor, wherein corrective action is automatically taken by the system if a test value is not inside a desired range to ensure the parameters for optimal production are kept within the desired range.

15. The method of claim 12, further comprising transmitting the data to a server.

16. The method of claim 12, wherein the stationary phase is an affinity chromatography stationary phase comprising a protein.

17. The method of claim 16 wherein the protein comprises an antibody.

18. The method of claim 16 wherein the protein comprises an antigen.

* * * * *